US00PP27665P2

(12) United States Plant Patent
Lan

(10) Patent No.: US PP27,665 P2
(45) Date of Patent: Feb. 14, 2017

(54) ***CLEMATIS* PLANT NAMED 'HJJ-HAZ01'**

(50) Latin Name: ***Clematis* hybrid**
Varietal Denomination: HJJ-HAZ01

(71) Applicant: Tsang Mei Lan, Au Tau (HK)

(72) Inventor: Tsang Mei Lan, Au Tau (HK)

( * ) Notice: Subject to any disclaimer, the term of this patent is extended or adjusted under 35 U.S.C. 154(b) by 0 days.

(21) Appl. No.: 14/756,999

(22) Filed: Nov. 5, 2015

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Cassandra Bright

(57) ABSTRACT

A new and distinct *Clematis* hybrid named 'HJJ-HAZ01' is disclosed, characterized by a unique non-vining plant habit. Plants are short and re-bloom multiple times during the Summer after pruning. Propagation is easy with a high rate of rooting success. Flowers have Violet colored tepals and yellow stamens. Flowers are positioned upward or outward. Plant habit is well suited for container plantings. The new cultivar is a *Clematis* typically suited for ornamental container and landscape use.

1 Drawing Sheet

Latin name of the genus and species: *Clematis* hybrid.
Variety denomination: 'HJJ-HAZ01'.

BACKGROUND OF THE INVENTION

The new cultivar is the result of a planned breeding program in Hoganas Sweden. The inventor is Tsang Mei Lan, a citizen of Hong Kong. The new variety was derived from the crossing of two unnamed, unpatented proprietary seedlings. The crossing resulting in the new cultivar was made during 2009. The new variety was discovered during 2010.

After selecting and isolating the new cultivar, asexual reproduction of the new cultivar 'HJJ-HAZ01' was first performed in Hong Kong, at a hobbyist nursery by vegetative cuttings in April 2012. 'HJJ-HAZ01' has since produced multiple generations, and has shown that the unique features of this cultivar are stable and reproduced true to type.

SUMMARY OF THE INVENTION

The cultivar 'HJJ-HAZ01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HJJ-HAZ01.' These characteristics in combination distinguish 'HJJ-HAZ01' as a new and distinct *Clematis* cultivar:

1. Unique plant habit: non-vining, suitable for a variety of garden and containers uses.
2. Re-blooming multiple times during the Spring and Summer after pruning.
3. Easy to propagate, with a high rate of success with rooting.
4. Short plants.
5. Dense plant habit due to short intermodal length 6. Flowers attractively positioned facing upward or outward
7. Violet flowers with contrasting yellow stamens.

PARENTAL COMPARISON

The new variety is similar to the seed parent in most horticultural characteristics, however plant of the new variety differ in the following:

1. The new variety has a non-vining habit, seed parent is vining.
2. The new variety blooms over a longer time period.
3. The new variety begins re-blooming sooner after pruning.
4. The new variety offers better performance in containers.
5. The new variety produces larger flowers.
6. The new variety produces flowers with a solid and consistent tepal color; parent variety shows variation in tepal color.
7. Flower attitude is more upward facing than parent variety.

The new variety is similar to the pollen parent in most horticultural characteristics, however plant of the new variety differ in the following:

1. The new variety is easier to propagate than the pollen parent, with greater success in rooting.
2. The new variety has more flexible plant stems, resisting breakage better.
3. The new variety begins re-blooming sooner after pruning.
4. The new variety is more compact and better suited for use in containers.
5. The new variety produces more flowers than the pollen parent.
6. Flower attitude is more upward facing than parent variety.

COMMERCIAL COMPARISON

Plants of the new cultivar 'HJJ-HAZ01' are similar to *Clematis durandii*, unpatented, in most horticultural characteristics. However, the new variety differs in the following:

1. The new variety is easier to propagate, with greater success in rooting.
2. The new variety begins re-blooming sooner after pruning.
3. The new variety is more compact and better suited for use in containers.
4. The new variety produces more flowers per plant
5. The new variety has more flexible plant stems, resisting breakage better.
6. The new variety produces violet colored tepals, whereas this comparator produces purple tepals.

The new variety can also be compared to *Clematis* 'Saphyra Indigo', unpatented, differing in the following characteristics:

1. The new variety has smaller flowers.
2. Tepals of the new variety are not undulating, compared to undulating tepals of 'Saphyra Indigo'.
3. The new variety produces stamens with a yellow color, stamens of the comparator are purple.
4. The new variety produces more flowers per plant, with a shorter intermodal length.
5. Tepal color of the new variety is Violet, color of the comparator is Blue.

BRIEF DESCRIPTION OF THE PHOTOGRAPH

The accompanying photograph in FIG. 1 illustrates in full color a typical plant of 'HJJ-HAZ01' grown outdoors in British Columbia, Canada.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'HJJ-HAZ01' plants grown outdoors in Japan. The growing temperature ranged from 8° C. to 20° C. at night and 10° C. to 30° C. during the day. No artificial light, photoperiodic treatments or chemical treatments were given to the plants. Plants were pinched once. Measurements and numerical values represent averages of typical flowering types.

Botanical classification: *Clematis* hybrid 'HJJ-HAZ01'.

Age of the plant described: Approximately 8 months.

Container size of the plant described: 3 liter.

PROPAGATION

Typical method: Vegetative cuttings.

Time to initiate root developments: 22-25 days in the summer at 32° C. to 33° C.

Time to produce a rooted cutting/young plant: 35-45 days in the summer at 32° C. to 33° C. 4 inch plant ready to flower.

Root description: Fine, fibrous.

PLANT

Growth habit and vigor:

*Growth habit*.—Herbaceous perennial plant, can be evergreen when growing in mild winter zone. Vigorous growth, non-climbing, stems are slender and erect. Mature stems might develop a sprawling habit when growing in semi-shaded or shaded location or if left unpruned after flowering.

*Time to produce a commercial plant*.—Approximately 6 months from an unrooted cutting to a.

*Height*.—Approximately 48 to 53 cm, measured from the soil after approximately 8 months. Unpruned plants can growth to 76 to 84 cm after flowering. Plant Spread: Approximately 53 to 76 cm.

*Growth rate*.—Approximately 15 to 20 cm per month during the growing season in the Summer.

*Branching characteristics*.—Freely branching at axillary nodes along stem.

*Length of main stem*.—Approximately 48 to 53 cm.

*Diameter of main stem*.—Approximately 0.2 cm.

*Main stem color*.—Near RHS Yellow-Green 146A.

*Main stem texture*.—Glabrous.

*Internode length*.—Varies from 3.5 to 8.0 cm.

*Strength*.—Strong, very flexible, semi-woody.

FOLIAGE

Leaf:

*Arrangement*.—Opposite, mainly single, rarely ternate near terminal flower.

*Average length*.—Approximately 7.6 cm.

*Average width*.—Approximately 5.1 cm.

*Shape of blade*.—Ovate to elliptic-ovate.

*Apex*.—Acuminate.

*Base*.—Attenuate.

*Attachment*.—Stalked.

*Margin*.—Entire. Rarely 1 to 3 large dentations.

*Texture upper and lower surfaces*.—Glabrous, slightly papery.

*Color*.—Young foliage upper side: Near RHS Yellow-Green 144A. Young foliage under side: Near RHS Yellow-Green 144A. Mature foliage upper side: Near RHS Green 137B. Mature foliage under side: Near RHS Green 137C.

*Venation*.—Type: Palmate, three main veins. Abaxially prominent. Venation color upper side: Near RHS Green 137C. Venation color under side: Near RHS Green 137C.

Petiole:

*Length*.—Approximately 1.0 to 1.5 cm.

*Diameter*.—Approximately 0.6 to 1 mm.

*Texture*.—Smooth.

*Color*.—Near RHS Green 137C.

FLOWER

Bloom period:

*Natural season*.—Begins flowering late Spring, with pruning plants begin re-blooming rapidly throughout Summer.

Inflorescence type and habit: 1 to 3 axillary occurring single flowers. 5 to 7 flowers per main stem. Average 1 to 3 flowers per lateral stem. Flowers facing upward or outward.

Rate of flower opening: Approximately 5 to 6 days from bud to fully opened flower.

Flower longevity on plant: Approximately 5 to 7 days, after fully opened. Self-cleaning.

Single flowers:

*Corolla*.—Tepal arrangement: 4 opposite tepals, forming a cross shape. Size: Length: Approximately 8.0 to 9.0 cm. Width: Approximately 1.5 to 1.8 cm. Margin: Entire. Apex: Acute to acuminate. Occasionally twisted at apex. Base: Blunt. Texture: Velvety, upper and lower surfaces.

Color:

*Tepals*.—When opening: Upper surface: Near RHS Violet 86A. Lower surface: Near RHS Violet 86C. Fully opened: Upper surface: Near RHS Violet N88A. Lower surface: Near RHS Violet N88A, mid rib near N87B. Ageing: Upper surface: Near RHS Violet N88B. Lower surface: Near RHS Violet N88C.

Bud:

*Shape*.—Conical, acuminate apex.
*Length*.—Average range 3 to 4 cm.
*Diameter*.—Approximately 0.8 cm.
*Color*.—Near RHS Violet 83A.

Peduncles:

*Length*.—Average range 5.0 to 6.5 cm.
*Width*.—Approximately 1 mm.
*Angle*.—Average 15°.
*Strength*.—Flexible.
*Color*.—Near RHS Green 137C.

Fragrance: None.

REPRODUCTIVE ORGANS

Stamens:

*Number*.—Average 38 to 50 per flower.
*Stamen color*.—Lower section near Violet N88A, upper section near Yellow 7D.
*Anther length*.—Approximately 3 mm.
*Anther color*.—Near RHS Yellow 12A.
*Anther shape*.—Linear.
*Pollen quantity*.—Abundant.
*Pollen color*.—Near RHS Yellow 4D.

Pistil:

*Quantity*.—Average 26 to 30 per flower.
*Length*.—Approximately 1.1 cm.
*Style length*.—Approximately 9 to 10 mm.
*Stigma*.—Shape: Linear. Color: Near RHS Yellow 4D.

OTHER CHARACTERISTICS

Seeds: Persistent. Typical average 30 seeds per flower. Round, approximately 1 mm diameter. Colored near RHS Green 137A.

Disease/pest resistance: Neither resistance nor susceptibility to normal pests of *Clematis* has been observed. Typical pests are Mealbybug and spider mites. Most common disease is powder mildew.

Temperature tolerance: Tolerates temperatures from approximately −26° C. to 38° C.

What is claimed is:

1. A new and distinct cultivar of *Clematis* hybrid plant named 'HJJ-HAZ01' as herein illustrated and described.

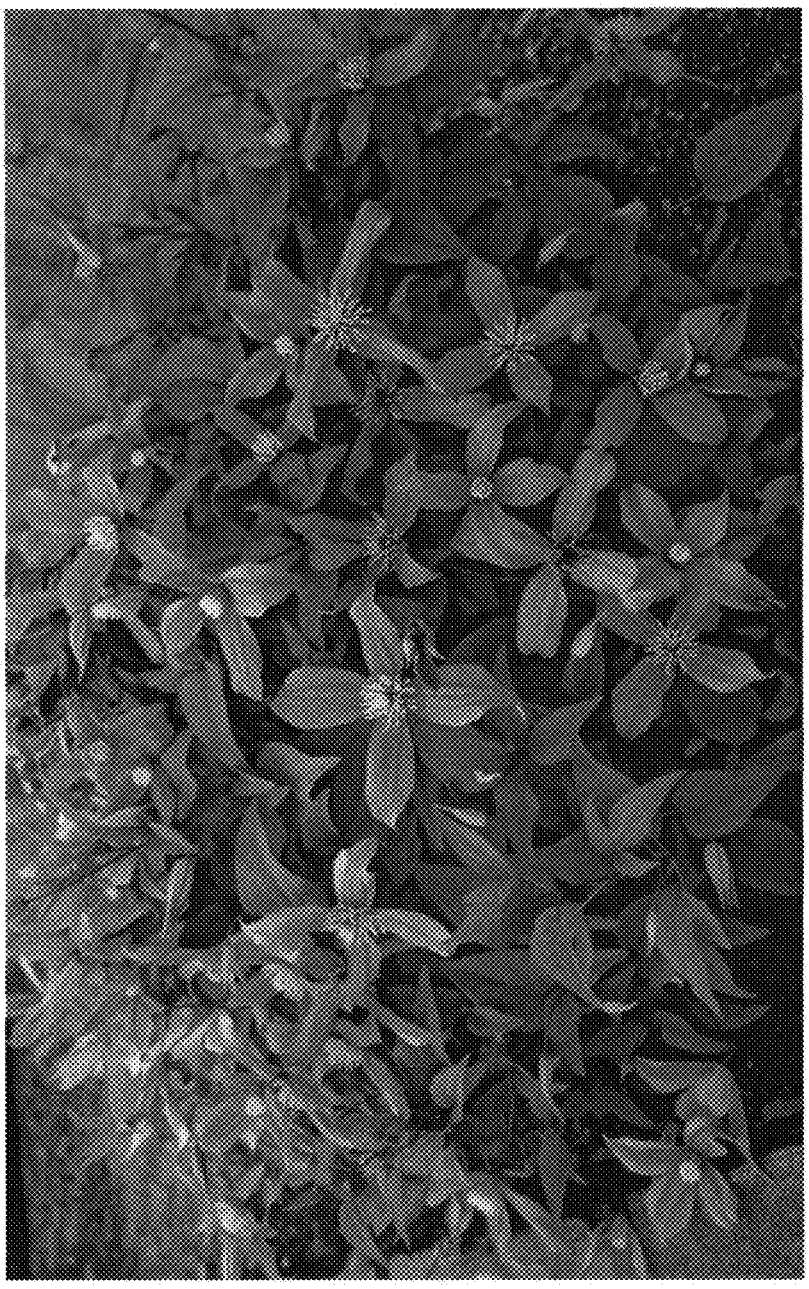

* * * * *